(12) United States Patent
Hurwitz

(10) Patent No.: US 8,728,446 B2
(45) Date of Patent: May 20, 2014

(54) ORAL HYGIENE TABLETS AND CAPSULES FOR DIRECT ORAL DELIVERY OF ACTIVE INGREDIENTS

(75) Inventor: Marni Markell Hurwitz, Far Hills, NJ (US)

(73) Assignee: I Did It, Inc., Far Hills, NJ (US)

( * ) Notice: Subject to any disclaimer, the term of this patent is extended or adjusted under 35 U.S.C. 154(b) by 232 days.

(21) Appl. No.: 12/156,609

(22) Filed: Jun. 3, 2008

(65) Prior Publication Data

US 2009/0297569 A1  Dec. 3, 2009

(51) Int. Cl.
*A61Q 11/00* (2006.01)

(52) U.S. Cl.
USPC ............... 424/49; 424/401; 424/52; 424/464

(58) Field of Classification Search
USPC ...................... 424/401, 49, 52, 464
See application file for complete search history.

(56) References Cited

U.S. PATENT DOCUMENTS

| | | | | |
|---|---|---|---|---|
| 3,772,431 | A | 11/1973 | Mlkvy et al. | 424/44 |
| 3,888,976 | A | 6/1975 | Mlkvy et al. | 424/44 |
| 3,962,417 | A * | 6/1976 | Howell | 424/52 |
| 4,259,355 | A | 3/1981 | Marmo et al. | 426/5 |
| 4,350,679 | A * | 9/1982 | Mizuno et al. | 424/456 |
| 4,816,259 | A * | 3/1989 | Matthews et al. | 424/463 |
| 4,865,481 | A | 9/1989 | Scales | 410/195 |
| 4,935,243 | A * | 6/1990 | Borkan et al. | 424/441 |
| 5,002,189 | A | 3/1991 | Sahi | 229/123.2 |
| 5,032,411 | A | 7/1991 | Stray-Gundersen | 426/74 |
| 5,057,305 | A | 10/1991 | Aberg | 424/44 |
| 5,114,723 | A | 5/1992 | Stray-Gundersen | 426/74 |
| 5,332,096 | A | 7/1994 | Battaglia | 206/532 |
| 5,609,897 | A | 3/1997 | Chandler | 426/73 |
| 5,681,606 | A | 10/1997 | Hutchison et al. | 426/590 |
| 6,022,528 | A * | 2/2000 | Waterfield et al. | 424/49 |
| 6,244,470 | B1 | 6/2001 | Harley-Wilmot | 111/153.14 |
| 6,287,596 | B1 | 9/2001 | Murakami et al. | 424/464 |
| 6,805,262 | B1 | 10/2004 | Frazier | 222/108 |
| 6,814,261 | B1 | 11/2004 | Gebrayel | 222/181.3 |
| 2001/0002252 | A1 * | 5/2001 | Gallopo et al. | 424/49 |
| 2002/0114767 | A1 | 8/2002 | Rolla | 424/49 |
| 2005/0260141 | A1 * | 11/2005 | Alexander | 424/49 |
| 2006/0002971 | A1 * | 1/2006 | Saltzman et al. | 424/423 |

OTHER PUBLICATIONS http://www.biovolutions.com/formulationdevelopment.htm#Drug Delivery, May 9, 2006.*

* cited by examiner

*Primary Examiner* — Lezah Roberts
*Assistant Examiner* — Tracy Liu
(74) *Attorney, Agent, or Firm* — Ernest D. Buff & Associates LLC; Ernest D. Buff; Harry Anagnost

(57) ABSTRACT

An oral hygiene tablet or capsule for direct oral delivery of active ingredients to humans and animals is provided composed of a tablet or capsule having an outer shell and inner cavity containing an active ingredient. Active ingredients contained and delivered by the oral hygiene tablet include mouthwash, toothpaste, medicament, mouth soothing and numbing agents, fluoride rinse, joint preserving agents, vitamins and herbal supplements. Other ingredients, such as flavor enhancers, scents, colorings and sugars may be included in the composition of the tablet or capsule. Delivery of the supplement ingredients is effectuated by simply placing the tablet into the mouth and allowing saliva to cause the outer shell to dissolve. The dissolution process can be accelerated by biting of the tablet/capsule and breaking it into smaller particles and/or by drinking water when the tablet is inserted into the mouth.

9 Claims, 4 Drawing Sheets

ORAL HYGIENE TABLETS AND CAPSULES FOR DIRECT ORAL DELIVERY OF ACTIVE INGREDIENTS

BACKGROUND OF THE INVENTION

1. Field of the Invention

The present invention relates to oral hygiene tablets and capsules appointed to release active ingredients directly into a person, pet or livestock's mouth and method of use; and, more particularly, to oral hygiene tablets and capsules containing active ingredients therein including, mouthwash, toothpaste, medicament, mouth soothing and numbing agents, fluoride rinse, joint preserving agents, vitamins and herbal supplements.

2. Description of the Prior Art

Travel is becoming increasingly difficult with restrictions being placed on airline bag weight, bag check number limitations, and issues concerning liquids located in carryon baggage. Currently available mouthwashes and toothpastes are generally sold in ranging sized containers, extending from large bottles or tubes to smaller travel size bottles and tubes. When traveling, large tubes and bottles can be quite cumbersome, taking up far too much space in one's luggage or carryon. Even still, the smaller bottles or tubes can be a nuisance as they generally only hold a small amount and are exhausted relatively quickly in the course of a vacation, requiring one to pack several small bottles or tubes. Thus, large bottles and containers of mouthwash or tubes of toothpaste prove to be quite cumbersome.

The vast majority of mouthwash products provide various types of packaging for mouthwash, generally composed of a polymeric material in the form of a container appointed for multiple servings therefrom. These types of large containers include measured quantity dispenser devices, such as that disclosed by U.S. Pat. No. 6,244,470 to Harley-Wilmot; U.S. Pat. No. 6,805,262 to Frazier; and U.S. Pat. No. 6,814,261 to Gebrayel. These larger containers with multiple servings therein are too cumbersome to pack or carry when traveling or the like, and they do not provide capsule delivery directly into the oral cavity.

One-time use packages of mouthwash have been provided, generally in the form of a small container with a single use measured amount of mouthwash therein, that is dispensed from the container, including that disclosed by U.S. Pat. No. 5,002,189 to Sahi and U.S. Pat. No. 4,865,481 to Scales. Although appointed for single use, these devices do not provide a capsule with mouthwash and/or toothpaste therein for direct delivery and dissolution into the mouth.

Generally where various mouthwash tablets have been provided, the tablets do not provide a direct delivery of mouthwash or toothpaste, but instead provide tablets or powder that are appointed to be mixed with water or other ingredients to form a mouthwash at the time of use. Including that disclosed by: U.S. Pat. Nos. 3,772,431 and 3,888,976 to Mlkvy, et al.; and U.S. Patent App. Publ. 20020114767 to Rolla. Likewise, many patents address issues related to providing nutritional supplements in a powder form, pill form or mixture appointed for addition to a beverage. Foe examples: U.S. Pat. Nos. 5,032,411, 5,114,723 to Stray-Gundersen; U.S. Pat. No. 5,609,897 to Chandler, et al.; U.S. Pat. No. 5,681,606 to Hutchison, et al.; U.S. Pat. No. 6,287,596 to Murakami, et al. However, these various tablets and nutritional supplements do not provide direct oral delivery by way of a tablet or capsule placed in the mouth, but instead provide for dissolution in a liquid vessel which is then drank by the user.

Even where mouthwash capsules have been provided, the mouthwash capsules do not provide a water soluble capsule with an oil based mouthwash housed therein, in a dosage equilibrated with that utilized to rinse one's mouth. For example, U.S. Pat. No. 5,332,096 to Battaglia discloses a mouthwash capsule including a water soluble gel capsule having a fluid mouthwash therewithin arranged in a packaging and opening structure in association with the capsule structure. However, the mouthwash is not oil based mouthwash, but instead is disclosed effervescent type tablets with active ingredients therein.

Moreover, various toothpaste chewing gums and tablets forming a paste upon chewing have been provided. For example, see U.S. Pat. No. 4,259,355 to Marmo, et al.; and U.S. Pat. No. 5,057,305 to Aberg. These gums and chewing tablets are not appointed to be utilized in conjunction with a toothbrush and are not provided as encapsulated toothpaste.

There have been several breath fresheners and breath refreshment gums offered on the market, but these products do not provide mouthwashes and do not provide toothpaste. Rather, they are merely bite sized mint candies appointed for freshening ones breath, and are not appointed to replace ones mouthwash and cannot be utilized as toothpaste.

There remains a need in the art for an oral hygiene capsule and tablet appointed to release ingredients directly into a person or pet's mouth and method of use thereof. More particularly, there is a need in the art for oral hygiene tablets and/or capsules containing ingredients therein including; mouthwash, toothpaste, medicament, mouth soothing and numbing agents, fluoride rinse, joint preserving agents, vitamins and herbal supplements, that are directly released into the user's mouth. Specifically, there remains a need in the art for an oral hygiene capsule/tablet appointed to contain a dosage of mouthwash or toothpaste and/or active ingredients so that a user can compactly carry and store mouthwash, toothpaste and/or active ingredients. Additionally, there is a need in the art for a mouthwash capsule comprising a gel capsule with an essential oil based mouthwash housed therein for direct delivery into a user's mouth. Further, there is a need in the art for a toothpaste tablet comprising a gel-like outer coating with toothpaste housed therein for direct delivery into a user's mouth for brushing.

SUMMARY OF THE INVENTION

The present invention is directed to an oral hygiene/supplement tablet or capsule preferably appointed to be dissolved in saliva and/or water in the mouth of a person or animal to deliver active ingredients orally. The oral hygiene/supplement tablet or capsule may be arranged as a capsule, with a gelatin, gelatin mixture, organogel, or other capsule ingredients, to encapsulate the active ingredients therein. Preferably, the capsule rapidly dissolves in the user's mouth to deliver the active ingredients. In another embodiment, the oral hygiene tablet includes an outer shell composed of a pressed powder with binders and includes effervescent properties so that it readily dissolves in an effervescent effect, dispersing the ingredients in the user's mouth.

The oral hygiene/supplement tablet or capsule includes active ingredients housed within an inner cavity protected by an outer shell. These active ingredients comprise: mouthwash, toothpaste, medicament, mouth soothing and numbing agents, fluoride rinse, joint preserving agents, vitamins and herbal supplements. Other ingredients, such as flavor enhancers, scents, colorings and sugars may be included in the composition of the tablet or capsule. Delivery of the supplement ingredients is effectuated by simply placing the tablet into the mouth and allowing saliva to cause the outer shell to dissolve. The dissolution process can be accelerated by biting of the tablet/capsule and breaking it into smaller particles and/or by drinking water when the tablet is inserted into the mouth.

In one embodiment, an oral hygiene tablet for direct oral delivery is provided including an outer shell and an inner cavity with active ingredients container there within. The outer shell is appointed to dissolve or break down in saliva in a mouth of a user, and may be hastened by drinking water at the time of insertion, or by biting and chewing on the outer shell to cause penetration and breakdown of the outer shell into small particles. Active-ingredients contained within the inner cavity of the tablet are released as the outer shell dissolves or is penetrated, and directly infuses the mouth and oral tissue to deliver the active ingredients within the oral cavity. Active ingredients include: toothpaste, hydrogen peroxide, mouthwash, herbal ingredients for providing a soothing effect to the mouth, numbing agents; vitamin and mineral compositions, medicinal agents, joint supplements, and/or a fluoride supplement. The outer shell of the tablet may be composed of effervescent ingredients comprising a mixture of citric acid and sodium bicarbonate as in a compressed powder form with binders, a gelatin composition to microencapsulate the active ingredients, a combination of gelatin and glycerin, a coating agent, a plant-based gelling substance like carrageenans and modified forms of starch and cellulose, an organogel, and/or a gum compound. Preferably, the oral hygiene tablet is sold or dispensed in a peel away package with a plurality of individual tablet compartments for individually housing the oral hygiene tablets therein, and has particular applications in compact storage and as travel tablets.

In another embodiment, an oral hygiene capsule for direct oral delivery is provided that comprises an outer shell and an inner cavity housing active ingredients therein. In this embodiment the outer shell is appointed to be discarded after it is opened and manipulated to release and directly deliver the active ingredients into a mouth of a user.

Further, an oral hygiene system is provided. The system includes a package including one or more peel away compartments each housing an oral hygiene tablet or capsule therein. The oral hygiene tablet or capsule comprises an outer shell and an inner cavity. The inner cavity container and housed active ingredients that are appointed to be directly delivered to a user's oral cavity whence released from the outer shell. Release from the outer shell is achieved by dissolving the outer shell in saliva in a mouth of a user.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

The present invention is directed to an oral hygiene/supplement tablet or capsule preferably appointed to be dissolved in saliva and/or water in the mouth of a person or animal to deliver active ingredients orally. The oral hygiene/supplement tablet or capsule may be arranged as a capsule, with a gelatin, gelatin mixture, organogel, or other capsule ingredients, to encapsulate the active ingredients therein. Preferably, the capsule rapidly dissolves in the user's mouth to deliver the active ingredients. In another embodiment, the oral hygiene tablet includes an outer shell composed of a pressed powder with binders and includes effervescent properties so that it readily dissolves in an effervescent effect, dispersing the ingredients in the user's mouth.

There are several advantages obtained by including active ingredients within a tablet or capsule having a water soluble/saliva soluble outer shell. Such oral hygiene/supplement tablets provide a unique, novel system for safe carriage of active ingredients, such as toothpaste and mouthwash, during travel, while also providing compact storage. Both the toothpaste tabs and mouthwash tabs, as well as other active ingredient tabs herein, address problems prevalent in the travel industry. In the modern day travel environment carried-on items are seriously evaluated and liquids can only be of a predetermined quantity, otherwise they are discarded by security. Sizing means so much when traveling with toiletries. The oral hygiene/supplement tablet uniquely addresses this recurring, ever increasing problem, and helps to eliminate stress associated with traveling.

Moreover, in today's hustle and bustle society, compacting everyday items and electronics is becoming increasingly important to the consumer. The oral hygiene/supplement tablets provide consumer the ability to purchase multiple packages of tablets having various active ingredients therein, in a compact unique way that allows for compact storage and easy carrying. For example, where the oral hygiene tablet herein is a toothpaste tablet, the user simply can carry the toothpaste tablets to work, or a restaurant, so that the user can readily brush his/her teeth after meals or eating, without the necessity to deal with a tube of tooth paste. Moreover, the tablets can be presented in combinations—so that a package of tablets include equal number of toothpaste tablets and mouthwash tablets so that the user can brush his/her teeth, and then rinse with the mouthwash tablet for an overall exceptionally hygienic experience.

Figure 1:
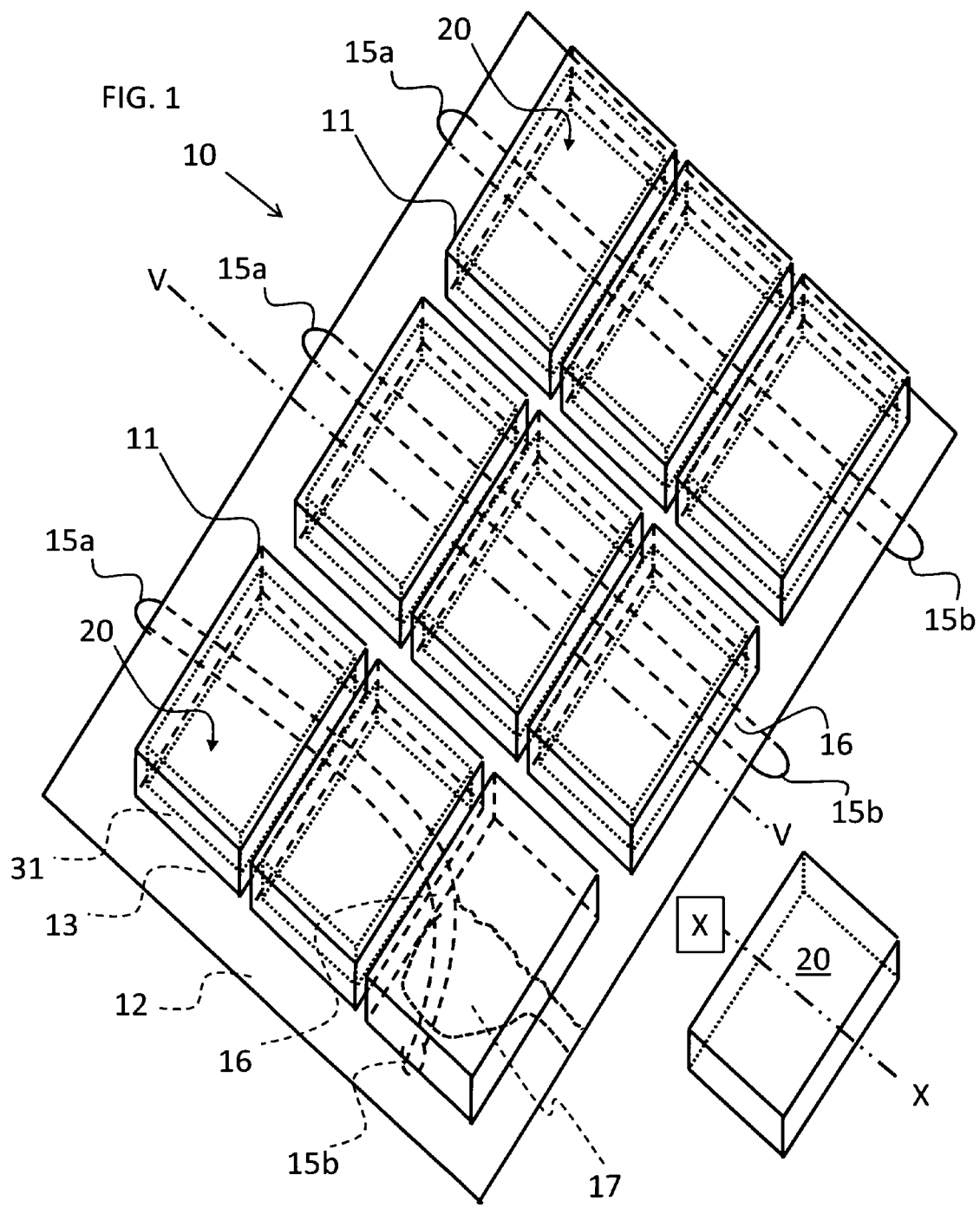
FIG. 1 is a schematic view of a peel away package with a plurality of individual tablet compartments individually housing oral hygiene tablets therein, wherein the peel away package comprises tab portions for readily accessing each of the individual tablet compartments and an oral hygiene tablet is shown removed from one of the compartment and ready for use.
Figure 2:
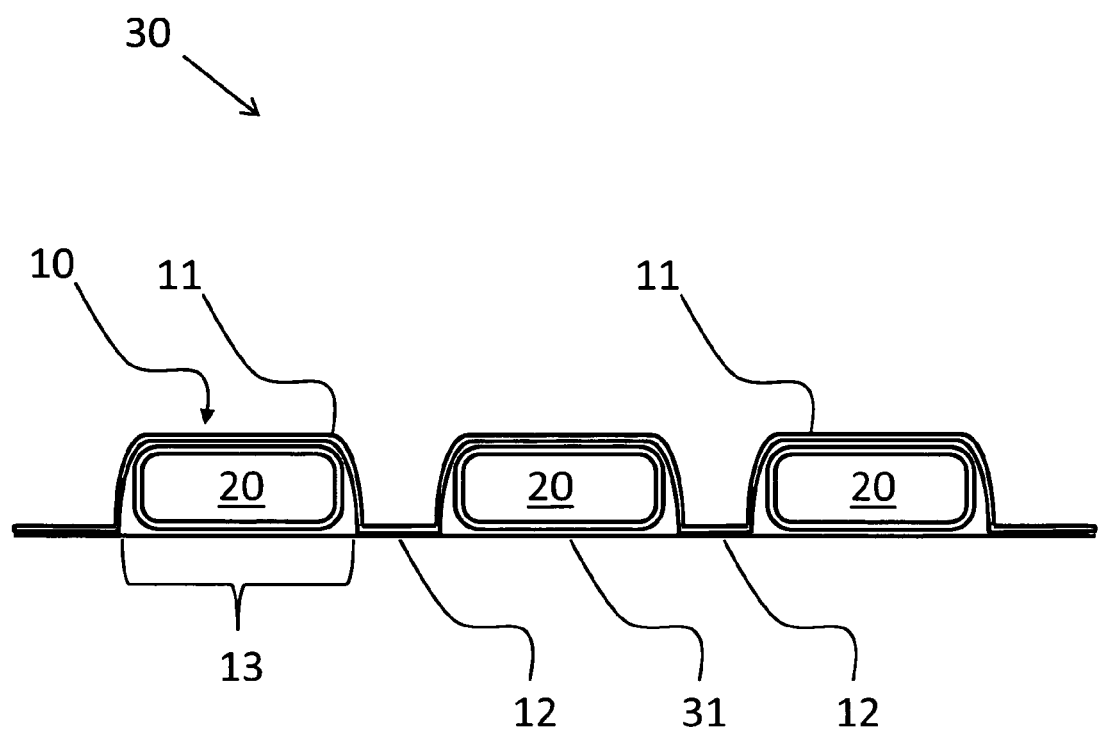
FIG. 2 is a cross-sectional view of the package of FIG. 1, taken along planer line V.

FIG. 1 is a schematic view of a peel away package with a plurality of individual tablet compartments housing oral hygiene tablets therein, shown generally at 10. FIG. 2 is a cross-sectional view of the package of FIG. 1, taken along planer line V, shown generally at 30. In referring to FIGS. 1 and 2, package 10 includes one or more peel away compartments 11 each housing an oral hygiene tablet/capsule 20 therein. Package 10 is generally comprised as a flexible, polymeric package with compartments 11 molded therein, with a flat under surface 12, and compartment apertures 13 for each compartment 11. A foil 31, or other covering, extends over flat under surface 12 of package 10, extending over each compartment aperture 13 to secure oral hygiene tablet 20 within compartment 11 during storage and before use. In the embodiment shown, package 10 comprises tab portions 15*a*, 15b with strip 16 therebetween. As shown, when tab portion 15b (or 15a) is pulled, strip 16 cuts through foil 31 to form an opening 17 which is further torn by the user for accessing compartment 11 and oral hygiene tablet 20 therein for removal of tablet 20.

Figure 3:
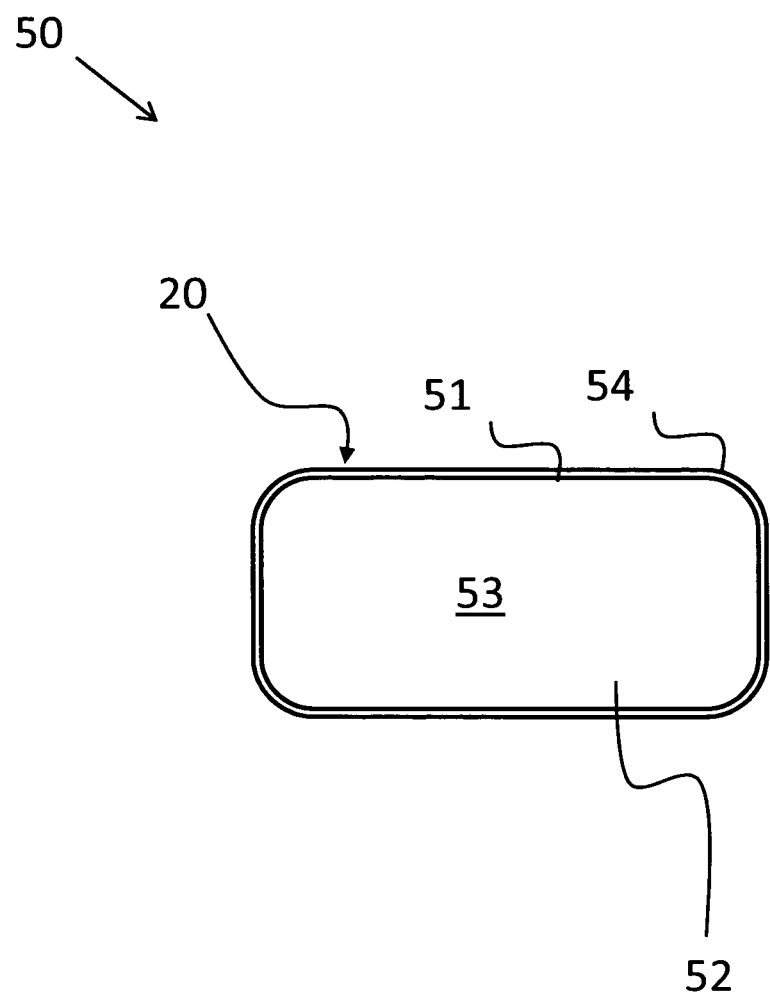
FIG. 3 is a cross-sectional view of the oral hygiene tablet or capsule of FIG. 1, taken along planer line X.

FIG. 3 is a cross-sectional view of the oral hygiene tablet or capsule of FIG. 1, taken along planer line X, shown generally at 50. Oral hygiene tablet 20 or capsule comprises an outer shell 51 and an inner cavity 52 containing active ingredients 53. Outer shell 51 preferably further comprises a coating agent 54, including carnauba wax to yield a glossy finish and enhanced protection of outer shell 51 from moisture during storage. Outer shell 51 is appointed to rapidly dissolve in saliva in a mouth of a user to deliver active ingredients 53 to the mouth of the user. Outer shell 51 is appointed to dissolve or break down in saliva in a mouth of a user, and may be hastened by drinking water at the time of insertion, or by biting and chewing on the outer shell to cause penetration and breakdown of the outer shell into small particles. Outer shell 51 (and coating agent 54) is preferably very thin, just providing enough coverage to protect and/or encapsulate active ingredients 53 therein. Active ingredients 53 contained within inner cavity 52 of tablet 20 are released as outer shell 51 dissolves or is penetrated, and directly infuses the mouth and oral tissue to deliver active ingredients 53 within the oral cavity.

The tablet is composed of a mixture of supplement ingredients, citric acid and sodium bicarbonate, and flavorings, pressed or compacted into a tablet form. Excipients, or inactive ingredients, may be included, such as water soluble binders; sweeteners or flavors; pigments to make tablets visually attractive; and effervescent enabling ingredients (such as citric acid and sodium bicarbonate). A soluble coating may be applied to provide taste, or to make it more resistant to the environment, extending its shelf life. A wide variety of binders may be used, including starch, cellulose, lactose powder, dibasic calcium phosphate, sucrose, corn (maize) starch, microcrystalline cellulose and modified cellulose (for example hydroxymethyl cellulose), and/or sorbital.

In one embodiment, outer shell 51 is composed of effervescent ingredients comprising a mixture of citric acid and sodium bicarbonate so that outer shell 51 rapidly effervescently dissolves in the mouth to release the active ingredients 53. In this manner, active ingredients 53 preferably are a chewable paste (such as toothpaste) or powder rather than a liquid. Ingredients utilized to form an effervescent outer shell 51 include a mixture of citric acid and sodium bicarbonate, which, when exposed to saliva and water drank in conjunction with the tablet to undergo chemical reaction to yield carbon dioxide and sodium citrate. Powdery ingredients may be pulverized to a fine mesh particle size to enable compression into tablet form, while having large enough surface area for quick dissolution when in water/when dropped in the liquid. For example 100 mesh particles have an average diameter of 140 microns while a 325 mesh particles have a diameter of only 44 microns thereby presenting a larger surface area. A 5 micron particle size results in a significantly larger surface area available for dissolution. Liquid or sticky ingredients may be microencapsulated in the effervescent tablets, which are free flowing or readily dissolving.

Wherein tablet 20 is a capsule type delivery method, outer shell 51 is composed of a gelatin composition. More preferably, outer shell 51 is composed of a combination of gelatin and glycerin (2% or less), mineral oil (2% or less). Outer shell 51 may comprise a coating agent, including carnauba wax to provide a glossy finish and enhance protection of outer shell 51 from the environment. A plant-based gelling substance like carrageenans and modified forms of starch and cellulose may be used to form outer shell 51 in forming the capsule 20. An organogel may be utilized forming outer shell 51, comprising non-crystalline, non-glassy thermoreversible solid materials composed of a liquid organic, such as an organic solvent, a mineral oil or a vegetable oil. The solubility and particle dimensions of the structurant are important characteristics for the elastic properties and firmness of the organogel. Preferably, the capsule is an oral quick-dissolving seamless capsule having thin walls. Such as that indicated by U.S. Pat. No. 7,025,911; or through various capsule preparation techniques. See publication "Microencapsulation" by Herbig as presented in the "Encyclopedia of Chemical Technology" of Kirk-Othmer, Volume 13, 2nd Edition, pp 436-456. Optionally, outer shell 51 is composed of a gum compound. Outer shell 51 may be soft or brittle so that it is bitten into smaller particles for more rapid dissolution in the mouth. In another embodiment, outer shell 51 is not soluble and therefore is not dissolved in the mouth, but instead is a polymeric material (thin and flexible) that is broken, cut or penetrated to release active ingredients in liquid form, which are dumped into the mouth and outer shell 51 discarded into a trash receptacle.

Active ingredient 53 may be a toothpaste and, preferably, outer shell 51 is a gel-like substance (i.e. organogel) that dissolves to release the toothpaste into the mouth so that the user can utilize a toothbrush implement in conjunction with the toothpaste to brush teeth. Preferably, the toothpaste is an essential oil and herbal toothpaste, for example, including extracts of Neem, Clove, Babool, Majuphal, Catechu and other herbs and natural extracts, as well as oils of coriander, ginger, lemon, and spearmint among other essential natural oils. The toothpaste is an amount suitable for brushing teeth of the user, ranging from 0.25 to 0.5 ounces. Alternatively, the toothpaste is a liquid composed of a hydrogen peroxide for cleaning and whitening the teeth.

Active ingredient 53 may be a mouthwash, preferably provided in an amount suitable for rinsing the oral cavity of the user, preferably ranging from 0.25 to 0.5 ounces. Wherein the active ingredient 53 is a mouthwash of liquid form, the outer shell of tablet 20 is formed as a capsule to contain the liquid and prevent leakage. Composition of the capsule is that as discussed hereinabove, in utilizing common capsule manufacturing processes. In order to prevent dissolution of outer shell 51 when the liquid mouthwash/active ingredient 53 during storage and before use, preferably the mouthwash is an essential oil based mouthwash rather than an alcohol based mouthwash as the alcohol would cause the capsule to degrade and dissolve. Preferably the mouthwash is essential oil based mouthwash comprising tea tree oil, alone or in combination with other essential oils, such as essential oil of spearmint (such as that sold under the trademark DESERT ESSENCE®, Tea Tree Oil Mouthwash). Other active ingredients, such as herbal ingredients for providing a soothing effect to the mouth, such as menthol, extract of piper cubeba, glycyrrhiza glabra, acorus calamus alpinia galanga, aloe vera gel, goldenseal, calendula, blood root, grapefruit seed extract, flavors (natural), citric acid, echinacea, chamomile, and vitamin b12. Such herbal ingredients, particularly aloe vera gel, goldenseal, calendula and blood root aid in protecting the gums and mouth tissue, while soothing same from irritants and temporarily relieving sore throat pain or discomfort. Numbing agents, such as clove oil (small amount), chamomilla 3×HPUS, benozocaine (7.5% or less), belladonna 3×HPUS (0.0003% Alkaloids)—for redness and inflammation, may be utilized to aid in providing comfort to the gums, oral tissue and/or teeth of the user.

Oral hygiene tablet/capsule 20 may further comprise a nutritional ingredient, including a vitamin composition and/or a mineral composition. Alternatively, the nutritional ingredient may be an electrolyte composition. Preferably, the vitamin composition includes vitamin A, vitamin B1, B2, B6, B12, vitamin C, vitamin E and coenzyme (CQ10). Typical vitamins in powder form includes vitamin C, B1, B2, B6, B12, folic acid coenzyme (CQ10) and D. Typical liquid or semi-solid vitamins include vitamin A and E. Mineral compositions may include calcium compounds, preferably calcium citrate, magnesium compound, preferably magnesium Citrate, chromium compound, preferably chromium picolinate or Niacin chromium GTF complex, zinc compound, selenium compound, iron compounds and others. Anti-oxidants include coenzymes. Hydrating substances include sodium and potassium chloride. Composition of the tablet may include at least one of a flavor enhancing ingredient and a taste enhancing ingredient. Flavor enhancing ingredients preferably include orange flavor, lemon or lime flavor, guava flavor, mango flavor, dragon fruit flavor, green tea, caffeine and guarana, peach flavor, or strawberry flavor. Alternatively, the tablet includes the taste enhancing ingredients of sweetener, sugars, pectin, fruit juice (in powder concentrate form) and an acidifier. Additionally, the ingredients may comprise at least one medically effective agent, such as gum Arabic powder. Gum Arabic is a natural product, occurring as an exudate from the trunks and branches of the Acacia Senegal tree. Gum Arabic power is water soluble. A six ounce dosage is sufficient to support an adult for twenty-four hours. In some cases of disease, it is considered that a solution of Gum Arabic may for a time constitute the exclusive drink and food of the patient. Active ingredient 53 may comprise a fluoride rinse or paste appointed to deliver a fluoride coating onto teeth.

Applications of the oral hygiene tablet can be used in treatment of people or in the veterinarian field for treatment of animals, such as pets, livestock and equine. In application to animals, medicaments, such as worm medication, nutrients, vitamins and supplements can be administered orally to the animal, in their drinking water, or chopped up and added to their food. Further, joint supplements may be added to the oral hygiene tablet to provide a pet supplement formulation designed to provide vitamins and minerals, as well as formula components that protect and/or build joint tissue. The joint building ingredient chicken collagen type II is selected to have a small molecular chain with a molecular weight in the range of 5,500 to 10,000. Another joint building ingredient, glucosamine sulfate for example, needs a substantial quantity of ascorbic acid or vitamin C. However, the vitamin C of the composition is exhausted by the oxidation process of the glucosamine sulfate. More vitamin C is needed for the general upkeep of the pet. Trace copper is needed for cross-linking cartilage tissue and is provided in the mineral content in biologically usable form as chelates. The anti-oxidants provided prevent free radical damage, a key factor in preserving joints. The formulation is provided generally in the form of a chewable tablet and contains a fixed quantity of these nutritional ingredients intimately mixed in a dry form. Providing proper dosage of this nutritional formulation to a pet based on its weight is extremely important. The tablets are thus marked for a given weight size such as a 35 kilogram dog and is readily cut and proportioned according to the actual weight of the pet being treated. The formulation shown below is designed for an animal weighing 35 kilograms and has the following active ingredients.

| Joint preserving/building components | |
|---|---|
| Chicken collagen (as collagen type II) | 500-1800 mg |
| Glucosamine hydrochloride | 500-3500 mg |
| Chondroitin sulfate | 500-1500 mg |

| Vitamin components | |
|---|---|
| Vitamin C (as ascorbic acid) | 100-1500 mg |
| Vitamin D (as cholecalciforal) | 100-400 IU |
| Vitamin K (as phylloquinone) | 10-40 mcg |

| Mineral components | |
|---|---|
| Calcium (as calcium carbonate, calcium citrate, malate glycinate) | 400-600 mg |
| Magnesium (as Magnesium oxide magnesium glycinate) | 300-500 mg |
| Zinc (as zinc glycinate) | 10-20 mg |
| Copper (as copper glycinate) | 1-4 mg |
| Manganese (as manganese glycinate) | 3-8 mg |
| Boron (from Boron chelate) | 1-3 mg |
| Herbal cofactor blend | 300-1000 mg | comprising citrus bioflavonoids, red grapes anthocyanins (vitis vinifera) (skin), turmeric rhizome (curcuma longa), boswellia resin (boswella serrata) and fennel seed (Foeniculum Vulgare).

The formulation may contain inactive ingredients such as microcrystalline cellulose, croscamellose sodium, silica, magnesium stearate, pharmaceutical glaze and other ingredients that improve processability of the composition and the texture of the final product.

The preferred composition is set forth below.

| Joint preserving/building components | |
|---|---|
| Chicken collagen (as collagen type II) | 800 mg |
| Glucosamine hydrochloride | 1500 mg |
| Chondroitin sulfate | 1200 mg |

| Vitamin components | |
|---|---|
| Vitamin C (as ascorbic acid) | 100 mg |
| Vitamin D (as cholecalciforal) | 200 IU |
| Vitamin K (as phylloquinone) | 20 mcg |

| Mineral components | |
|---|---|
| Calcium (as calcium carbonate, calcium citrate, malate glycinate) | 500 mg |
| Magnesium (as Magnesium oxide magnesium glycinate) | 400 mg |
| Zinc (as zinc glycinate) | 15 mg |
| Copper (as copper glycinate) | 2 mg |
| Manganese (as manganese glycinate) | 5 mg |
| Boron (from Boron chelate) | 1.5 mg |
| Herbal cofactor blend | 500 mg |

Including citrus bioflavonoids, red grapes anthocyanins (vitis vinifera) (skin), turmeric rhizome (curcuma longa), boswellia resin (boswella serrata) and fennel seed (Foeniculum Vulgare). The formulation may contain inactive ingredients such as microcrystalline cellulose, croscamellose sodium, silica, magnesium stearate, pharmaceutical glaze and other ingredients that improve processability of the composition and the texture of the final product.

Figure 4:
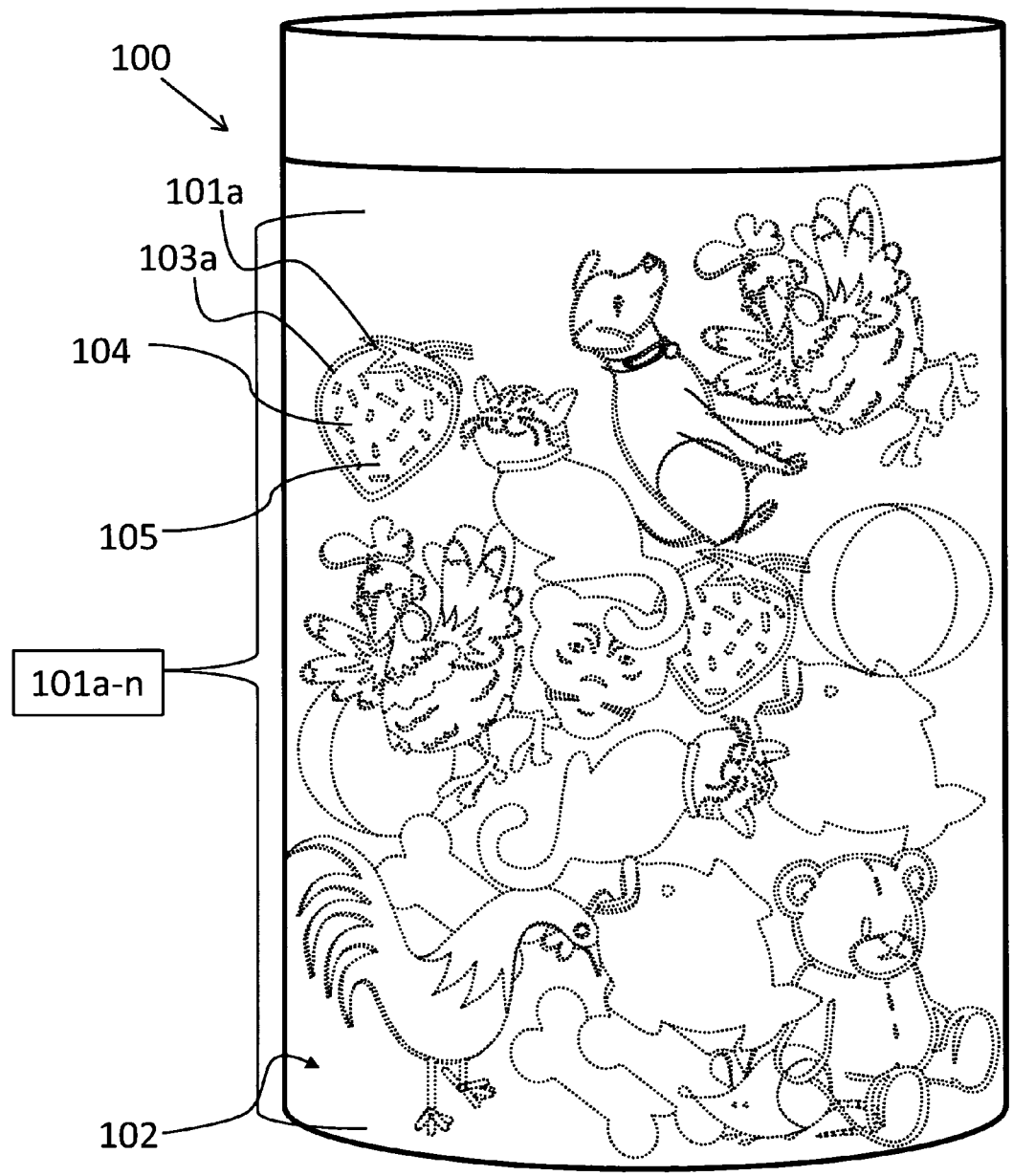
FIG. 4 is a schematic view of a container of oral hygiene tablets and/or capsules wherein the outer shell (and visa vie the tablet and/or capsule) is shaped in a variety of shapes and sizes.

FIG. 4 is a schematic view of a container of oral hygiene tablets and/or capsules wherein the outer shell (and visa vie the tablet and/or capsule) is shaped in a variety of shapes and sizes, shown generally at 100. Oral hygiene tablets 101 (101a-n) are shown housed in a container 102, and are configured so that the outer shell 103 of tablets 101 are of a plethora of shapes comprising a shape in form of an animal, creature, toy, object or character (specifically pointing to 101a, 103a as a representative shaped tablet 101). As constructed, oral hygiene tablet 101 include outer shell 103 with an inner cavity 104 containing active ingredients 105 therein, as shown by way of tablet 101a. The oral hygiene tablets and capsules may be of a plethora of shapes, including parallelograms in general, circles, ovals, and combinations of same. Further, these oral hygiene tablets and capsules may be formed in the shape of animals or creatures, toys, and other objects to yield imaginary animal and object shaped oral hygiene tablets and capsules, as shown. These imaginary animals and objects would be appealing to children, and would encourage use of the oral hygiene tablets and capsules by children and teenagers, at camp, on trips, college and the like. The animal and object shaped oral hygiene tablets and capsules could be packaged in the manner previously described (i.e. in a packet having discrete compartments therein as shown in the aforediscussed FIGS. 1 and 2), or stored in a bottle or like vessel so that the creatures and imaginary objects would be visible to young people, thereby encouraging usage, improving nutrition and proper dental hygiene.

Continuing with FIG. 4, preferably, the outer shell 103 of the shaped tablets 101 comprises a gum agent for yielding a chewing gum when chewed on by a child or young adult. As such, the tablets provide a chewing gum that does not offer benefits derived from active ingredients 105 therein, inducing vitamins, supplements, toothpaste, fluoride, mouthwash, whiteners, etc. The tablets 101a-n may be of different shapes, sizes and/or colors—and may be demarcated via color, for example, to illustrate different active ingredient 105 characteristics within a specifically colored/shaped tablet 101a-n so that container 102 may contain a variety of tablets 101a-n having a variety of different active ingredients 105a-n therein. These features are appointed to have particular applications in encouraging young children to take their vitamins, fluoride or the like, or to be excited about brushing their teeth. Shapes shown in container 102 via tablets 101a-n are merely representative, but a plethora of different shapes may be provided. The animal shaped tablets 101a-n can be well known characters or trademarks to aid in attracting children while providing a marketing tool for companies owning the character or/and trademark or brand image. Container 102 may be a typical container, box, cartridge, decorative dispenser, or other type of container, such as that discussed in reference to FIGS. 1 and 2.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An oral hygiene tablet for direct oral delivery comprising an outer shell and an inner cavity
   a. wherein said outer shell comprises gelatin; glycerin; organogel; effervescent ingredients comprising a mixture of citric acid and sodium bicarbonate; a plant-based gelling substance selected from the group consisting of carrageenans, modified forms of starch, and cellulose; and carnauba wax as a coating agent; and
   b. wherein said inner cavity comprises an amount of toothpaste, for brushing the teeth of a user, ranging from 0.25 to 0.5 ounces, said toothpaste comprising hydrogen peroxide and fluoride that delivers a fluoride coating onto said teeth; and
   whereby said outer shell is in a shape of an animal, creature, toy or character and will dissolve or break down in saliva in a mouth of a user to directly deliver said toothpaste to said user during consumption or said mouth so that said user can utilize a toothbrush implement.

2. An oral hygiene tablet as recited by claim 1, wherein said toothpaste further comprises a vitamin and/or mineral.

3. An oral hygiene tablet as recited by claim 2, wherein said vitamin is selected from the group consisting of vitamin A, vitamin B1, B2, B6, B12, vitamin C, vitamin E, coenzyme (CQ10) and mixtures thereof.

4. An oral hygiene tablet as recited by claim 2, wherein said mineral is selected from the group consisting of a calcium compound, magnesium compound, chromium compound, zinc compound, selenium compound, iron compound and mixtures thereof.

5. An oral hygiene tablet as recited by claim 1, wherein said toothpaste further comprises at least one medically effective agent.

6. An oral hygiene tablet as recited by claim 5, wherein said medically effective agent is Gum Arabic.

7. An oral hygiene tablet as recited by claim 1, wherein said toothpaste further comprises joint supplements.

8. A peel away package with a plurality of individual tablet compartments for individually housing the oral hygiene tablets of claim 1.

9. The peel away package as recited by claim 8, wherein said peel away package comprises tab portions for readily accessing each of said individual tablet compartments.

* * * * *